United States Patent
Westritschnig et al.

(10) Patent No.: US 7,425,333 B2
(45) Date of Patent: Sep. 16, 2008

(54) HYPOALLERGENIC ALLERGY VACCINES BASED ON THE TIMOTHY GRASS POLLEN ALLERGEN PHL P 7

(75) Inventors: Kerstin Westritschnig, Vienna (AT); Margarete Focke, Vienna (AT); Anna Twardosz, Baden (AT); Peter Valent, Vienna (AT); Petra Verdino, Graz (AT); Walter Keller, Judendorf (AT); Dietrich Kraft, Vienna (AT); Rudolf Valenta, Theresienfeld (AT)

(73) Assignee: Biomay Produktions-und Handels-Aktiengesellschaft, Vienna (AT)

( * ) Notice: Subject to any disclaimer, the term of this patent is extended or adjusted under 35 U.S.C. 154(b) by 443 days.

(21) Appl. No.: 10/529,441

(22) PCT Filed: Sep. 25, 2003

(86) PCT No.: PCT/EP03/10701

§ 371 (c)(1), (2), (4) Date: Aug. 3, 2005

(87) PCT Pub. No.: WO2004/029083

PCT Pub. Date: Apr. 8, 2004

(65) Prior Publication Data

US 2006/0216314 A1    Sep. 28, 2006

(30) Foreign Application Priority Data

Sep. 27, 2002    (EP) .................................. 02021837

(51) Int. Cl.
| | |
|---|---|
| *A01N 37/18* | (2006.01) |
| *A61K 38/00* | (2006.01) |
| *A61K 39/00* | (2006.01) |
| *A61K 39/35* | (2006.01) |
| *A61K 39/36* | (2006.01) |
| *C07K 2/00* | (2006.01) |
| *C07K 4/00* | (2006.01) |
| *C07K 5/00* | (2006.01) |
| *C07K 7/00* | (2006.01) |
| *C07K 14/00* | (2006.01) |
| *C07K 16/00* | (2006.01) |
| *C07K 17/00* | (2006.01) |

(52) U.S. Cl. ..................... 424/185.1; 424/275.1; 514/2; 530/300

(58) Field of Classification Search ....................... None
See application file for complete search history.

(56) References Cited

FOREIGN PATENT DOCUMENTS

| WO | WO 99/34826 A1 | 7/1999 |
|---|---|---|
| WO | WO-1999/34826 | * 7/1999 |
| WO | WO 99/38978 A1 | 8/1999 |

OTHER PUBLICATIONS

Fatima Ferreira et al., "Modulation of IgE reactivity of allergens by site-directed mutagesis: potential use of hypoallergenic variants for immunotherapy", The FASEB Journal, Feb. 1998, pp. 231-242, vol. 12.

Verena Niederberger et al., "Calcium-dependent immunoglobulin E recognition of the apo- and calcium-bound form of a cross-reactive two EF-hand timothy grass pollen allergen, Phl p7", The FASEB Journal, May 1999, pp. 843-856, vol. 13.

Cenk Suphioglu et al, "Molecular cloning and immunological characterization of Cyn d 7, a novel calcium-binding allergen from Bermuda grass pollen", FEBS Letters, 1997, pp. 167-172, vol. 402.

Susanne Vrtala et al., "Conversion pf the Major Birch Pollen Allergen, Bet v 1, into Two Nonanaphylactic T Cell Epitope-containing Fragments", Journal of Clinical Investigation, 1997, pp. 1673-1681, Vo. 99, No. 7.

* cited by examiner

*Primary Examiner*—Maher M. Haddad
*Assistant Examiner*—Nora M Rooney
(74) *Attorney, Agent, or Firm*—Chalin Smith; Smith Patent Consulting, LLC

(57) ABSTRACT

The present invention pertains to polypeptides derived from the timothy grass pollen allergen Phl p 7. The polypeptides display reduced allergen activity and are useful as allergy vaccines for treatment of sensitized allergic patients and for prophylactic vaccination.

5 Claims, 10 Drawing Sheets

Figure 6 (Table 1)

Figure 1:
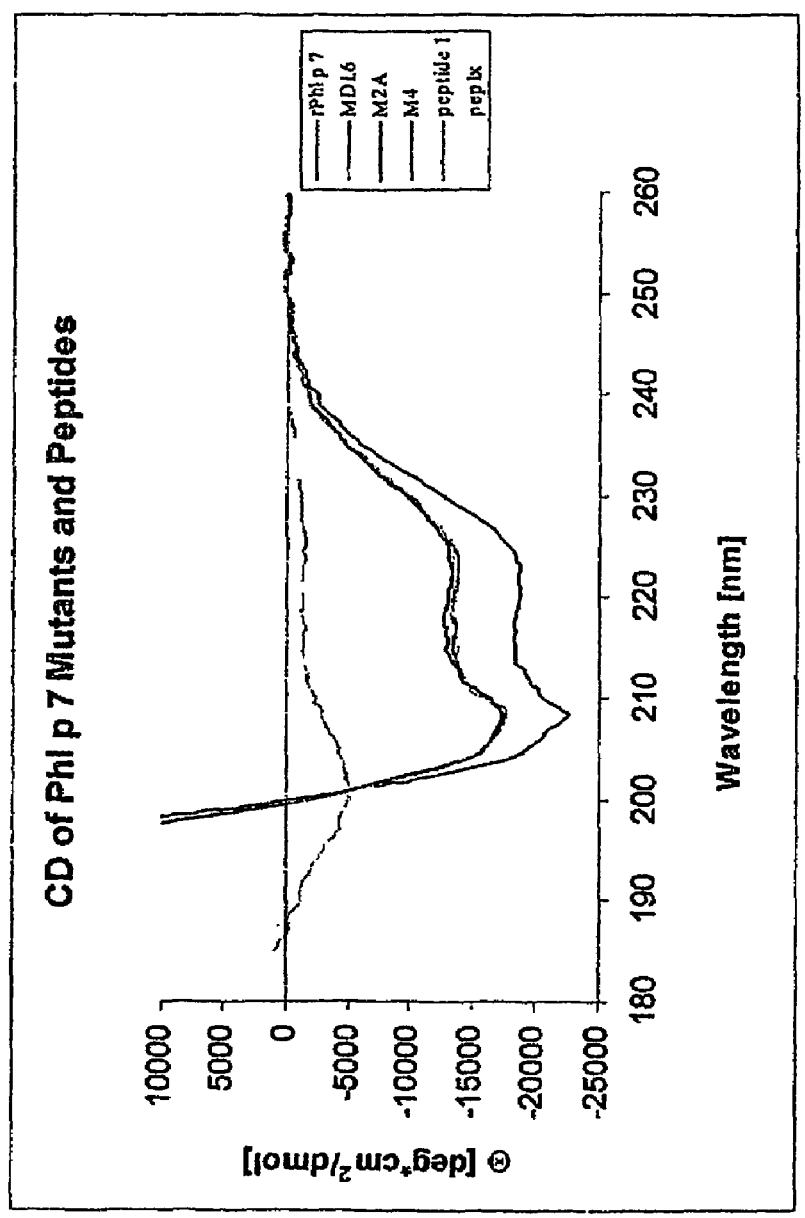

Characteristics of non-allergenic Phl p 7-derived synthetic peptides and Phl p 7-derived mutants

| | Position aa | Sequence | Number of aa | Molecular weight | Isoelectric Point (pI) | Fold (CD) |
|---|---|---|---|---|---|---|
| Peptide 1 | 2-37 | ADDMERIFKRFDTNGDGKISLSELTDALRTLGSTSA | 36 | 3932 | 4.40 | - |
| Peptide 2 | 36-78 | SADEVQRMMAEIDTDGDGFIDFNEFISFCNANPGLM KDVAKVF | 43 | 4701.9 | 3.71 | - |
| Mutant 1.6 | 1-78 | MADDMERIFKRFDTNGDGKISLSALTDALRTLGSTSA DEVQRMMAEIDTDGDGFIDFNAFISFCNANPGLMKD VAKVF | 78 | 8559.9 | 4.08 | + |
| M

Figure 7 (Table 2)

Induction of immediate skin reactions with rPhl p 7 and Phl p 7-derived peptides and mutant

| Individual | rPhl p 7 | | timothy grass | histamine | mean wheal diameter | | | | | |
|---|---|---|---|---|---|---|---|---|---|---|
| | 2µg/ml | 8µg/ml | | | P1 | | P2 | | M4 | |
| | | | | | 1µg/ml | 4µg/ml | 1µg/ml | 4µg/ml | 2µg/ml | 8µg/ml |
| 1 | 8 | 11 | 10 | 4 | 0 | 0 | 0 | 0 | 7 | 9 |
| 2 | 5 | 8 | 10 | 3 | 0 | 0 | 0 | 0 | 4 | 5 |
| 3 | 6 | 9 | 5 | 4 | 0 | 0 | 0 | 0 | 9 | 7 |
| 4 | 0 | 0 | 0 | 5 | 0 | 0 | 0 | 0 | 0 | 0 |

Figure 8 (Table 3)

Rabbit anti-Phl p 7 peptide antisera and a rabbit anti-Phl p 7 mutant antiserum inhibit serum IgE binding of grass pollen allergic patients to rPhl p 7

| Patient | % inhibition | | | | |
|---|---|---|---|---|---|
| | anti-P1 | anti-P2 | anti-M4 | anti-M4-KLH | anti-rPhl p 7 |
| 1 | 0 | 64.8 | 0 | 35.8 | 82 |
| 2 | 0 | 42.26 | 2.7 | 18.95 | 83.7 |
| 3 | 0 | 42.2 | 19.9 | 4 | 79 |
| 4 | 9.4 | 39.1 | 0 | 35.2 | 64.1 |
| mean | 2.35 | 47.9 | 5.6 | 23.4 | 77.2 |

Figure 9

```
Phl p 7:  1  MADD-------MERIFKRFDTNGDGKISLSELTDALRTLGSTSADEVQRMMAEIDTDGDG  53
             MADD       ERIFK FD NGDGKIS SEL DAL TLGS   DEV MMAEIDTDGDG
Aln g 4:  1  MADDHPQDQAEHERIFKCFDANGDGKISASELGDALKTLGSVTPDEVKHMMAEIDTDGDG  60

Phl p 7: 54  FIDFNEFISFCNANPGLMKDVAKVF  78
             FI F EF  F  AN GL KDVAK F
Aln g 4: 61  FISFQEFTNFARANRGLVKDVAKIF  85
```

HYPOALLERGENIC ALLERGY VACCINES BASED ON THE TIMOTHY GRASS POLLEN ALLERGEN PHL P 7

This application is a national stage of PCT/EP2003/010701, filed Sep. 25, 2003. The entire contents of the above-identified application are hereby incorporated by reference.

The present invention pertains to polypeptides derived from the timothy grass pollen allergen Phl p 7. The polypeptides display reduced allergenic activity and are useful as allergy vaccines for treatment of sensitized allergic patients and for prophylactic vaccination.

More than 25% of the population suffers from IgE-mediated allergies. The symptoms of allergy (allergic rhinoconjunctivitis, asthma, dermatitis, anaphylactic shock) are due to IgE recognition of allergens. In order to induce strong effector cell activation and thus inflammatory responses, an allergen must be able to cross-link effector cell-bound IgE antibodies efficiently. This process requires the presence of at least two IgE epitopes on the allergen surface. IgE antibodies of allergic patients may recognize either "continuous epitopes" consisting of a row of consecutive amino acids or "discontinuous epitopes" which are composed of amino acids from different portions of the allergen brought into proximity by the molecule fold. Allergen-induced cross-linking of mast cell-bound IgE antibodies induces the immediate release of biologically active mediators (e.g., histamine, leukotriens) whereas IgE-mediated presentation of allergens to T cells causes T cell activation and release of proinflammatory cytokines.

About 5-20% of pollen-allergic individuals are sensitized to a recently discovered group of calcium-binding proteins containing two binding sites for calcium. These pollen allergens are therefore termed two-EF hand pollen allergens. Due to sequence similarities these proteins contain cross-reactive IgE epitopes and sensitized patients show therefore allergic symptoms upon contact with a great variety of different pollens from trees, grasses and weeds.

Allergen-specific immunotherapy currently represents one of the few curative forms of therapy for IgE-mediated allergies. It is currently conducted by the administration of allergen-containing extracts to sensitized individuals, mostly by injection but also via other routes (e.g., sublingual immunotherapy). While pollen extracts from trees, grasses and weeds are standardized regarding certain major allergens, no standardization is performed regarding less frequently recognized but highly cross-reactive allergens, e.g., the above mentioned calcium-binding allergens.

Allergy to the two-EF hand pollen allergens can therefore not be sufficiently treated with crude allergen extracts. Furthermore, two-EF hand allergens are highly allergenic and upon injection may induce severe allergic side effects.

The invention aims at providing means for the prophylactic or therapeutic treatment of allergy to two-EF hand pollen allergens. It has been found that mutants of the timothy grass pollen allergen Phl p 7 show strongly reduced IgE binding and are thus useful as hypoallergenic agents. The amino acid sequence of Phl p 7 is shown in SEQ ID NO:1. The invention relates to a mutated polypeptide derived from the pollen allergen Phl p 7 selected from the group consisting of
(a) polypeptides comprising an amino acid sequence in which in respect to the amino acid sequence as shown in SEQ ID NO:1 one to 15 amino acid residues are deleted, substituted and/or added;
(b) polypeptides comprising a fragment of (a), wherein the fragment has a length of at least 15 amino acids and at least 90% of the amino acid residues of the fragment are identical to corresponding residues of the amino acid sequence as shown in SEQ ID NO:1;
(c) polypeptides comprising a fragment of the amino acid sequence as shown in SEQ ID NO:1, wherein the fragment has a length of at least 15 amino acids;
(d) polypeptides consisting of a fragment of (a), wherein the fragment has a length of at least 10 amino acids and at least 80% of the amino acid residues of the fragment are identical to corresponding residues of the amino acid sequence as shown in SEQ ID NO:1; and
(e) polypeptides consisting of a fragment of the amino acid sequence as shown in SEQ ID NO:1, wherein the fragment has a length of at least 10 amino acids;

wherein the mutated polypeptide has reduced IgE binding activity compared to wild type Phl p 7.

As used herein, the term "polypeptide" denotes a compound comprising at least 7 amino acids which are linked by peptide bonds. The polypeptide is preferably composed only of amino acids, but it may also comprise non-proteinaceous components. The length of the polypeptide is preferably at least 10 amino acids, more preferably at least 15 amino acids. The polypeptide may also be a fusion protein comprising a portion which is derived from Phl p 7 and a fusion partner. The portion derived from Phl p 7 may further be linked to a carrier molecule, e.g. keyhole limpet hemocyanin (KLH).

The term "two-EF hand pollen allergen" as used herein designates a calcium binding polypeptide, the amino acid sequence of which is at least 60% identical to the amino acid sequence as shown in SEQ ID NO:1. These polypeptides have amino acid sequences identical to the respective naturally occurring pollen allergens.

A "mutated" polypeptide according to the invention is a polypeptide the amino acid sequence of which is different from that of wild type or naturally occurring two-EF hand pollen allergens.

An amino acid substitution denotes the replacement of one amino acid with a different amino acid. Preferably, acidic residues are substituted. The substituting amino acid may be of any type, preferably it is a non-acidic amino acid, more preferably a hydrophobic amino acid such as alanine, valine, leucine, etc.

In one embodiment, the polypeptide of the invention comprises an amino acid sequence which has 1 to 15 amino acid deletions, substitutions and/or additions in respect to the amino acid sequence as shown in SEQ ID NO:1. Preferably, the number of amino acid deletions, substitutions and/or additions is 1 to 10, more preferably 1 to 6, most preferably 1 to 4. The polypeptides of this embodiment are at least 63 amino acids in length, the preferred length is about 78 amino acids. The preferred polypeptides have 1, 2, 3 or 4 amino acid substitutions in respect to the amino acid sequence as shown in SEQ ID NO:1. More preferably the polypeptide comprises an amino acid sequence in which in respect to the amino acid sequence as shown in SEQ ID NO:1 the amino acids at position 24 and 59, more preferably at position 17, 24 and 59, even more preferably at position 17, 24, 52 and 59 are substituted. The most preferred polypeptides comprise an amino acid sequence as shown in SEQ ID NO:4, SEQ ID NO:5 or SEQ ID NO:6. The polypeptide represented by SEQ ID NO:4 carries two mutations as compared with the amino acid sequence as shown in SEQ ID NO:1, namely E24A and D59A. The polypeptide represented by SEQ ID NO:5 has the mutations D17A, E24A, D59A as compared with SEQ ID NO:1. The polypeptide represented by SEQ ID NO:6 carries mutations D17A, E24A, D52A and E59A as compared with SEQ ID NO:1.

The invention further concerns polypeptides comprising a fragment of the polypeptides described above (a). The fragment has a length of at least 15 amino acids, i.e. it consists of at least 15 consecutive amino acids of the polypeptide described above (a). Preferably, the length of the fragment is at least 20 amino acids, more preferably at least 25 amino acids, even more preferably at least 30 amino acids. At least 90% of the amino acid residues of the fragment are identical to corresponding residues of the amino acid sequence as shown in SEQ ID NO:1, preferably at least 92%, most preferably at least 95%. Percent sequence identity is determined by conventional methods. The degree of identity of the amino acid sequence of the fragment to SEQ ID NO:1 may be determined by comparing the amino acid sequence of the fragment and SEQ ID NO:1 using the program "Blast 2 sequences version Blast p2.1.2" (Tatusova et al. (1999) FEMS Microbiol. Lett. 174, 247-250). The parameters which are used in this context are: matrix: BLOSUM 62; gap open: 11; gap extension: 1; X drop off: 50; expect: 10; word size: 3; filter: no.

In another embodiment, the polypeptide of the invention comprises a fragment of the amino acid sequence as shown in SEQ ID NO:1 with a length of at least 15 amino acids. The fragment consists of at least 15 consecutive amino acids of the amino acid sequence as shown in SEQ ID NO:1, preferably at least 20 consecutive amino acids, more preferably at least 25 consecutive amino acids, most preferably at least 30 consecutive amino acids.

The polypeptides of the invention may also consist of a fragment of the polypeptides described above (a). This fragment consists of at least 10 consecutive amino acids of the polypeptide described above (a), preferably at least 15 consecutive amino acids, more preferably at least 20 consecutive amino acids, even more preferably at least 25 consecutive amino acids, most preferably at least 30 consecutive amino acids. The amino acid sequence of the fragment is at least 80% identical to corresponding residues of the amino acid sequence as shown in SEQ ID NO:1. The degree of amino acid sequence identity is determined as described supra. The sequence identity of the fragments to the amino acid sequence of SEQ ID NO:1 is preferably at least 85%, more preferably at least 90%, most preferably at least 95%.

In another embodiment, the polypeptide of the invention consists of a fragment of the amino acid sequence as shown in SEQ ID NO:1. This fragment consists of at least 10 consecutive amino acids of the amino acid sequence as shown in SEQ ID NO:1, preferably at least 15 consecutive amino acids, more preferably at least 20 consecutive amino acids, even more preferably 25 consecutive amino acids, most preferably at least 30 consecutive amino acids. Preferred polypeptides comprise at least the amino acids forming one of the EF hand motifs (amino acids D13-L25 or D48-F60 of the amino acid sequence as shown in SEQ ID NO:1). Examples are the polypeptides consisting substantially of the amino acid sequence as shown in SEQ ID NO:2 (first EF hand motif or SEQ ID NO:3 (second EF hand motif, respectively, optionally coupled to a carrier molecule such as KLH.

In accordance with the present invention, surface-exposed amino acids which potentially are involved in epitope formation may be substituted or deleted. It has been found that the highly conserved residues lysine 19 and phenylalanine 54 of SEQ ID NO:1 are solvent-exposed. Therefore, substitution or deletion of these residues may be carried out to obtain a polypeptide with reduced allergenic activity. Suggested mutations are the residues asparagine 15, glycine 16 and aspartic acid 17 of SEQ ID NO:1. These residues form a kind of uncharged cap on top of the N-terminal calcium-binding loop. Substitution of these residues (e.g. with charged amino acids) will result in a completely different surface pattern of this immunologically interesting protein region. Another target is the mutation of the residues aspartic acid 50, aspartic acid 52 and aspartic acid 56 of SEQ ID NO:1. These amino acids are responsible for a distinct negative charge distribution on the surface of the C-terminal calcium-binding loop. It was shown that a peptide consisting of the 12 amino acids forming the C-terminal calcium-binding loop is immunologically active. Thus, the mutation of the above mentioned aspartic acid residues will heavily influence this epitope. Furthermore, at least one of the amino acids within the uncharged ridge may be substituted or deleted. These are phenylalanine 57, asparagine 58, isoleucine 61, serine 62, asparagine 65, alanine 66, proline 68 and methionine 5 (which is provided from the opposite monomer chain) of SEQ ID NO:1.

It has further been found that recombinantly produced Phl p 7, which corresponds to naturally occurring Phl p 7, occurs as a novel dimer assembly adopting an extended conformation. Two protein monomers assemble in a head to tail arrangement with domain-swapped EF-hand pairing. The intertwined dimer adopts a barrel-like structure with an extended hydrophobic cavity providing a ligand-binding site. Calcium binding acts as a conformational switch between an open and a closed dimeric form of Phl p 7. Therefore, disruption of dimer assembly may be envisaged according to the invention. This strategy targets the high cross-linking activity of Phl p 7 on the effector cell-bound IgE antibodies. As a result of the domain swapping, the protein assembles into a highly symmetric dimer. This leads to the doubling of (identical) IgE epitopes. A conversion of the domain-swapped dimer into the corresponding monomer is expected to maintain the IgE epitopes but to strongly diminish the allergy-eliciting cross-linking activity. Therefore, according to the invention mutations of the hinge loop that destabilize the extended linker region between the N- and C-terminal calcium-binding domains is proposed. First mutation of at least one of the amino acids that provide the discrete hydrogen bonds and thus stabilize the rigid conformation of the linker region is suggested: these are the highly conserved residues arginine 30, glycine 33, serine 34, threonine 35, serine 36 and glutamic acid 39 (of SEQ ID NO:1). The exchange of these residues against amino acids that are unable to form hydrogen bonds (e.g. bulky non-polar amino acids) would strongly affect the stability of the hinge-loop conformation. Furthermore we suggest the substitution of the hinge loop forming residues (especially glycine 33, serine 34, threonine 35, serine 36) by a stretch of small flexible amino acids (such as glycine or alanine), either one by one or by introducing a longer stretch, elongating the hinge loop and simultaneously increasing its flexibility. Another possibility is the exchange of the short rigid Phl p 7 hinge loop (glycine 33, serine 34, threonine 35, serine 36) with corresponding loop-forming sequences known from intra-domain paired EF-hand proteins. All these mutations enable the formation of a monomeric Phl p 7 with intramolecular EF-hand pairing.

Furthermore, the dimeric structure may be disrupted by mutation of at least one of the hydrophobic residues that provide interaction between the E-helices and the Z-helix of the opposite monomer in the domain-swapped dimer. These amino acids are isoleucine 8, phenylalanine 12 (part of the N-terminal E-helix), threonine 35, valine 40, methionine 43 and isoleucine 47 (part of the C-terminal E-helix), as well as the residues methionine 71, valine 74, alanine 75, lysine 76, valine 77 and phenylalanine 78 (part of the Z-helix) of SEQ ID NO:1. Mutation of these amino acids (e.g. by charged or bulky residues) will strongly destabilize the symmetric dimer assembly.

The polypeptides of the present invention have reduced allergenic activity compared to wild type Phl p 7. According to the invention the allergenic activity of a sample is determined by determining the IgE antibodies which are induced in a test animal upon application of the sample. The allergenic activity is preferably defined in suitable in vitro or in vivo tests. The allergenic activity may be determined in a skin test as described in van Hage-Hamsten et al. J. Allergy Clin. Immunol. 1999, 104, pp. 969-977 or in Pauli et al. Clin. Exp. Allergy 2000, 30, pp. 1076-1084. The allergenic activity of wild type Phl p 7 may be determined using recombinantly produced Phl p 7 consisting of the amino acid sequence as shown in SEQ ID NO:1.

Preferably the allergenic activity of the polypeptide is less than 50% of the allergenic activity of the wild type Phl p 7. More preferably the allergenic activity of the polypeptide is less than 25% of the wild type protein. In the most preferred embodiment the polypeptide has substantially no allergenic activity. Generally, the histamine release induced by the polypeptide of the invention is significantly reduced compared to the histamine release induced by Phl p 7. A preferred in vitro test for determining the histamine release is the basophil histamine release assay as described in Vrtala et al., J. Clin. Invest. 1997, 99, pp. 1673-1681. Preferably, the histamine release is reduced by at least 25%, more preferably by at least 50%, most preferably by at least 75%, determined at that concentration of allergen at which Phl p 7 shows maximum histamine release.

The polypeptides of the invention show reduced binding to IgE antibodies from timothy grass pollen allergic patients compared with wild type Phl p 7 (SEQ ID NO:1). The IgE binding activity is preferably reduced by at least 25%, more preferably by at least 50%, most preferably by at least 75%. Recombinant Phl p 7 consisting substantially of the amino acid sequence as shown in SEQ ID NO:1 can be used to determine the IgE binding activity of wild type Phl p 7. IgE binding of polypeptides may be determined by Western blot analysis or dot blot experiments using serum from a timothy grass pollen allergic patient. Timothy grass pollen allergy is diagnosed according to a case history indicative for timothy grass pollen allergy (i.e., seasonal symptoms of allergy during the flowering period of grasses), positive skin test reaction to timothy grass pollen allergens and/or the detection of specific IgE antibodies to timothy grass pollen allergens in serum. Dot blots can be quantified by measuring the amount of $^{125}$I-labeled anti-human IgE antibodies by gamma counting as described (Niederberger et al. J. Allergy Clin. Immunol. 1998, 102, 579-591).

It has also been found that the Phl p 7-derived polypeptides of the invention induce IgG antibody responses in vivo. Therefore, the polypeptides described above comprise at least one IgG epitope. A polypeptide comprises at least one IgG epitope when it is capable of eliciting an IgG antibody response in an individual or a test animal. A corresponding test for determining an IgG response is described in Example 3. More preferably, these IgG antibodies are "blocking antibodies" or "protective antibodies" which prevent IgE antibodies from binding to Phl p 7. A significant reduction of allergic symptoms may be achieved in this way.

It has been found that the polypeptides of the invention which carry mutations corresponding to the mutations represented by amino acid sequences SEQ ID NO:2, SEQ ID NO:3, SEQ ID NO:4, SEQ ID NO:5 or SEQ ID NO:6 have unexpected advantageous properties. The amino acid positions targeted in these amino acid sequences can be substituted or deleted in other 2-EF hand pollen allergens as well. Therefore, the present invention relates to a mutated polypeptide derived from a 2-EF hand pollen allergen, wherein in respect to the wild type sequence of the 2-EF hand pollen allergen amino acid positions have been substituted or deleted which correspond to the amino acid residues which are substituted or deleted in respect to SEQ ID NO:1 in SEQ ID NO:2, SEQ ID NO:3, SEQ ID NO:4, SEQ ID NO:5 or SEQ ID NO:6. The identification of amino acid positions in other 2-EF hand pollen allergens which correspond to the amino acid positions mutated in anyone of SEQ ID NO:2 to 6 is within the level of ordinary skill. For example, the skilled person may align anyone of the sequences as shown in SEQ ID NO:1 to 6 with the amino acid sequence of a given 2-EF hand pollen allergen using the program Blast 2 sequences described above. From the alignment the corresponding amino acid positions to be mutated can easily be derived. As an example, FIG. 9 shows an alignment of Phl p 7 and Aln g 4. The amino acid positions to be substituted or deleted correspond to D17, E24, D52 and/or E59 of SEQ ID NO:1. These positions correspond to D24, E31, D59 and E66 of the amino acid sequence of Aln g 4 (SEQ ID NO:7). The polypeptides derived from 2-EF hand pollen allergens may be comprised in a larger polypeptide or be coupled to a suitable carrier protein such as KLH. They also have reduced allergenic activity and IgE binding capacity compared with their respective wild type forms and are capable of inducing an IgG response as described supra. The amino acid sequences of several 2-EF hand pollen allergens are known:

Aln g 4 (alder) (Hayek et al. J. Immunol. 1998, 161, 7031-7039)

Cyn d 7 (Bermuda grass) (Suphioglu et al. FEBS Lett. 1997, 402,167-172)

Bra r 1 (rape-Brassica) (Toriyama et al. FEBS Lett. 1998, 424, 234-238)

Bet v 4 (birch) (Twardosz et al. Biochem. Biophys. Res. Commun. 1997, 239,197-204)

Ole e 3 (olive) (Ledesma et al. Eur. J. Biochem. 1998, 258, 454-459)

The amino acid sequences of Aln g 4, Cyn d 7, Ole e 3, Bet v 4 and Bra r 1 are shown in SEQ ID NO:7, SEQ ID NO:8, SEQ ID NO:9, SEQ ID NO:10 and SEQ ID NO:11, respectively. The amino acid at position 71 of SEQ ID NO:10 may also be alanine.

It is to be noted that polypeptides derived from 2-EF hand pollen allergens other than Phl p 7 are only claimed as far as they comprise substitutions or deletions at the same amino acid positions as SEQ ID NO:2 to 6.

The invention relates to a mutated polypeptide derived from Aln g 4, wherein in respect to the amino acid sequence as shown in SEQ ID NO:7 the amino acids at position 31 and 66, preferably at position 24, 31 and 66, more preferably at position 24, 31, 59 and 66 are substituted. The invention further relates to a polypeptide consisting substantially of amino acids 2 to 44 or 43 to 85 of SEQ ID NO:7, optionally coupled to a carrier molecule such as KLH.

Another aspect of the invention is a mutated polypeptide derived from Cyn d 7, wherein in respect to the amino acid sequence as shown in SEQ ID NO:8 the amino acids at position 26 and 61, preferably at position 19, 26 and 61, more preferably at position 19, 26, 54 and 61 are substituted. Another aspect is a polypeptide consisting substantially of amino acids 2 to 39 or 38 to 80 of the amino acid sequence as shown in SEQ ID NO:8, optionally coupled to a carrier molecule such as KLH.

In yet another aspect the invention relates to a mutated polypeptide derived from Ole e 3, wherein in respect to the amino acid sequence as shown in SEQ ID NO:9 the amino acids at position 30 and 65, preferably at position 23, 30 and 65, more preferably at position 23, 30, 58 and 65 are substituted. The invention also relates to a polypeptide consisting substantially of amino acids 2 to 43 or 42 to 84 of the amino acid sequence as shown in SEQ ID NO:9, optionally coupled to a carrier molecule such as KLH.

In yet another aspect the invention relates to a mutated polypeptide derived from Bet v 4, wherein in respect to the amino acid sequence as shown in SEQ ID NO:10 the amino acids at position 31 and 66, preferably at position 24, 31 and 66, more preferably at position 24, 31, 59 and 66 are substituted. The invention also relates to a polypeptide consisting substantially of amino acids 2 to 44 or 43 to 85 of the amino acid sequence as shown in SEQ ID NO:10, optionally coupled to a carrier molecule such as KLH.

In yet another aspect the invention relates to a mutated polypeptide derived from Bra r 1, wherein in respect to the amino acid sequence as shown in SEQ ID NO:11 the amino acids at position 25 and 60, preferably at position 18, 25 and 60, more preferably at position 18, 25, 53 and 60 are substituted. The invention also relates to a polypeptide consisting substantially of amino acids 2 to 38 or 37 to 79 of the amino acid sequence as shown in SEQ ID NO:11, optionally coupled to a carrier molecule such as KLH.

Wild type Phl p 7 represented by the amino acid sequence as shown in SEQ ID NO:1 and proteins comprising wild type Phl p 7 are not within the scope of the present invention. Naturally occurring 2-EF hand pollen allergens or recombinant proteins consisting of the same amino acids are not claimed in this application (e.g. Bet v 4, Bra r 1, Aln g 4, Cyn d 7, etc.).

The present invention also provides polynucleotide molecules, including DNA and RNA molecules, that encode the polypeptides disclosed herein. Those skilled in the art will readily recognize that, in view of the degeneracy of the genetic code, considerable sequence variation is possible among these polynucleotide molecules. The polynucleotide may be single or double-stranded. It is to be recognized that according to the present invention, when a polynucleotide is claimed as described herein, it is understood that what is claimed are both the sense strand, the antisense strand and the DNA as double-stranded having both the sense and antisense strand annealed together by their respective hydrogen bonds. Also claimed is the messenger RNA (mRNA) which encodes the polypeptides of the present invention. Messenger RNA will encode a polypeptide using the same codons as those used by DNA, with the exception that each thymine nucleotide (T) is replaced by a uracil nucleotide (U).

Methods for preparing DNA and RNA are well known in the art. A full-length clone encoding Phl p 7 can be obtained by conventional cloning procedures. The DNA encoding Phl p 7 may be amplified by polymerase chain reaction (PCR) employing suitable specific primers. The polynucleotides of the present invention may also be synthesized chemically, for example using the phosphoramidite method.

The invention further relates to a vector or plasmid containing a polynucleotide as described above. In general, the polynucleotide sequence encoding a polypeptide of the invention is operably linked to other genetic elements required for its expression, generally including a transcription promoter and terminator, within an expression vector. The vector will also commonly contain one or more selectable markers or one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

Another aspect of the invention is a host cell transformed or transfected with a vector or a plasmid according to the invention. The host cells may be prokaryotic or eukaryotic cells. Prokaryotic host cells, including strains of the bacteria *Escherichia coli*, Bacillus and other genera are useful host cells within the present invention. Techniques for transforming these hosts and expressing foreign DNA sequences cloned therein are well known in the art (see, e.g., Sambrook et al., Molecular Cloning, a Laboratory Manual, Cold Spring Harbor Laboratory, 1989).

The host cells of the invention may be used to produce the polypeptides of the invention. Yet another aspect of the invention therefore is a method of preparing a polypeptide according to the invention comprising culturing host cells described above under conditions that said polypeptide is expressed and optionally recovering said polypeptide from the host cells. When expressing a polypeptide of the invention in bacteria such as *E. coli*, the polypeptide may be retained in the cytoplasm, possibly as insoluble inclusion bodies. In this case, the cells are lysed and the inclusion bodies are recovered and denatured using, for example, guanidine isothiocyanate or urea. The denatured polypeptide can then be refolded by diluting the denaturant, such as by dialysis against a solution of urea and a combination of reduced and oxidized glutathione, followed by dialysis against a buffered saline solution.

Transformed or transfected host cells are cultured according to conventional procedures in culture medium containing nutrients and other components required for the growth of the chosen host cells. A variety of suitable media, including defined media and complex media, are known in the art and generally include a carbon source, a nitrogen source and minerals. It is preferred to purify the peptides of the present invention to $\geq 80\%$ purity, more preferably $\geq 95\%$ purity, and particularly preferred is a pharmaceutically pure state that is greater than 99.9% pure with respect to contaminating macromolecules, particularly other proteins and nucleic acids, and free of infectious and pyrogenic agents. Preferably, a purified polypeptide of the invention is substantially free of other polypeptides. Expressed recombinant polypeptide of the invention can be purified using fractionation and/or conventional purification methods and media. Ammonium sulfate precipitation and acid or chaotrop extraction may be used for fractionation of samples. The polypeptides of the invention may also be isolated by affinity chromatography using antibodies directed to the polypeptide. Shorter polypeptides are preferably purified using HPLC. Methods of protein purification are described e.g. in Methods in Enzymology, Volume 182. Guide to Protein Purification. Academic Press New York 1990 and Scopes, Protein Purification. Springer Verlag, Heidelberg 1994.

The polypeptides of the invention may also be prepared through chemical synthesis, for example, as described by Merryfield, J. Am. Chem. Soc. 85:2149, 1963 and Etherton et al., Solid Phase Peptide Synthesis: A Practical Approach, IRL Press, Oxford 1989.

The invention further relates to the use of the polypeptide of the invention for the manufacture of a medicament for treating and/or preventing an allergic disorder. The disorder usually is an allergy to one or more 2-EF hand pollen allergens, e.g. to Phl p 7. It has been found that Phl p 7 contains most of the relevant IgE epitopes of the family of 2-EF hand pollen allergens. Therefore, the polypeptides may be used in the treatment of allergies to almost any 2-EF hand pollen allergen. Preferably, the allergic disorder to be treated is allergy to at least one of the proteins Bet v 4, Bra r 1, Aln g 4, Bra n 1, Cyn d 7, Ole e 3, Syr v 3 and/or Phl p 7. The medicament may be used for the therapeutic treatment of an allergic disorder or for prophylactic vaccination to prevent development of the disorder.

The invention also pertains to a pharmaceutical composition comprising at least one polypeptide of the invention. The composition may further comprise a pharmaceutically acceptable carrier or diluent. Preferably, the polypeptide of the invention has been coupled to a carrier molecule such as KLH.

Another aspect of the invention is a pharmaceutical kit comprising at least one polypeptide of the invention. The kit may comprise two or more different polypeptides according to the present invention. In one embodiment the kit comprises at least one mutated polypeptide derived from Phl p 7 and at least one mutated polypeptide derived from another 2-EF hand pollen allergen. Other allergens from timothy grass pollen or from other pollen and their epitopes may be contained. In another aspect, the mutated polypeptide derived from Phl p 7 may be one component in a prophylactic pharmaceutical composition for vaccination containing the most important allergens from different allergen sources (mite, cat, pollen, mushrooms, etc.).

For pharmaceutical use, the polypeptides of the present invention are formulated for oral or parenteral, particularly subcutaneous, delivery according to conventional methods. In general, pharmaceutical formulations will include a polypeptide of the invention in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in Remington: The Science and Practice of Pharmacy, Gennaro, Ed., Mack Publishing Co., Easton, Pa., 19th Edition 1995. Therapeutic or prophylactic doses will generally be in the range of 0.1-100 µg per injection in a volume of 100-200 µl, with the exact dose determined by the physician according to accepted standards, taking into account the nature and severity of the condition to be treated, patient traits, etc. Determination of dose is within the level of ordinary skill in the art. The amount may vary depending on the mode of treatment. During immunotherapy treatment single doses of about 25 µg to 75 µg can be administered in a volume of about 100 µl per injection. In case of oral administration a dosage of 0.1 µg to 50 mg can be envisaged. In the case of vaccinations, patients are usually not treated several times a day except for "rush immunotherapy". Common immunotherapies include approximately 8 pre-seasonal vaccinations that are administered in intervals of one to two weeks and that are continued over a period of 2 to 3 years. Preferably, 4 injections per year with an interval of 3 months over 3 to 5 years are applied. In a particular embodiment, more than one polypeptide is contained in the pharmaceutical composition.

DESCRIPTION OF THE TABLES AND FIGURES

FIG. 1. CD spectra of Phl p 7, the Phl p 7-derived peptides and the Phl p 7-derived mutants (M1.6, M2A, M4).

Figure 2:
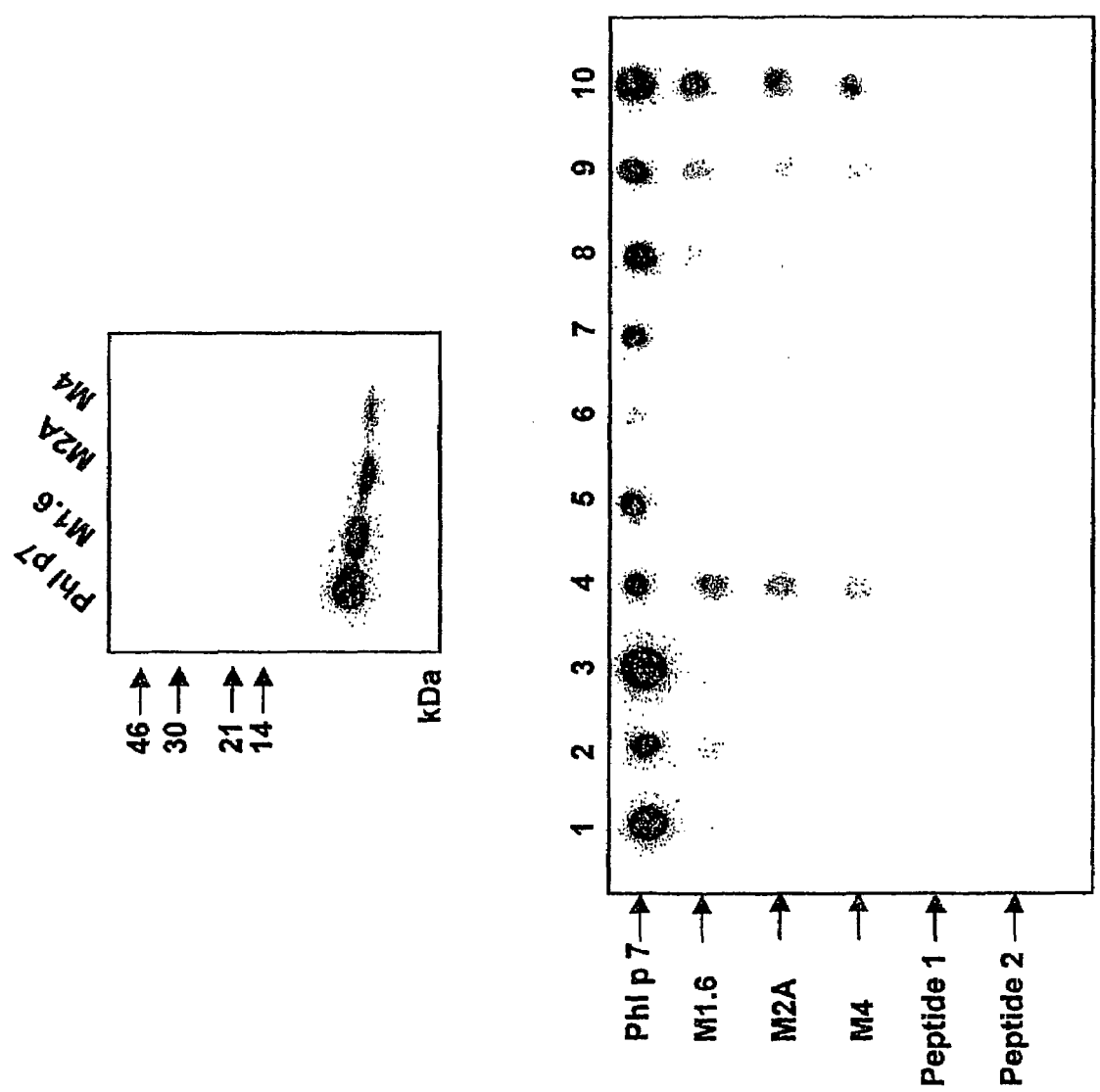

FIG. 2A, B. Reduction of the IgE binding capacity of Phl p 7-derived mutants and of Phl p 7-derived peptides.

Nitrocellulose blotted rPhl p 7 (lane Phl p 7) and rPhl p 7-derived mutants (lanes M1.6, M2A, M4) were probed with serum from a Phl p 7-sensitized grass pollen allergic patient. Bound IgE antibodies were detected with $^{125}$I-labeled anti human IgE antibodies (FIG. 2A). Nitrocellulose dotted Phl p 7 and Phl p 7-derived mutants (M1.6, M2A, M4) as well the Phl p 7-derived peptides were probed with sera from ten Phl p 7-sensitized grass pollen allergic patients. Bound IgE antibodies were detected with $^{125}$I-labeled anti human IgE antibodies (FIG. 2B).

Figure 3A:
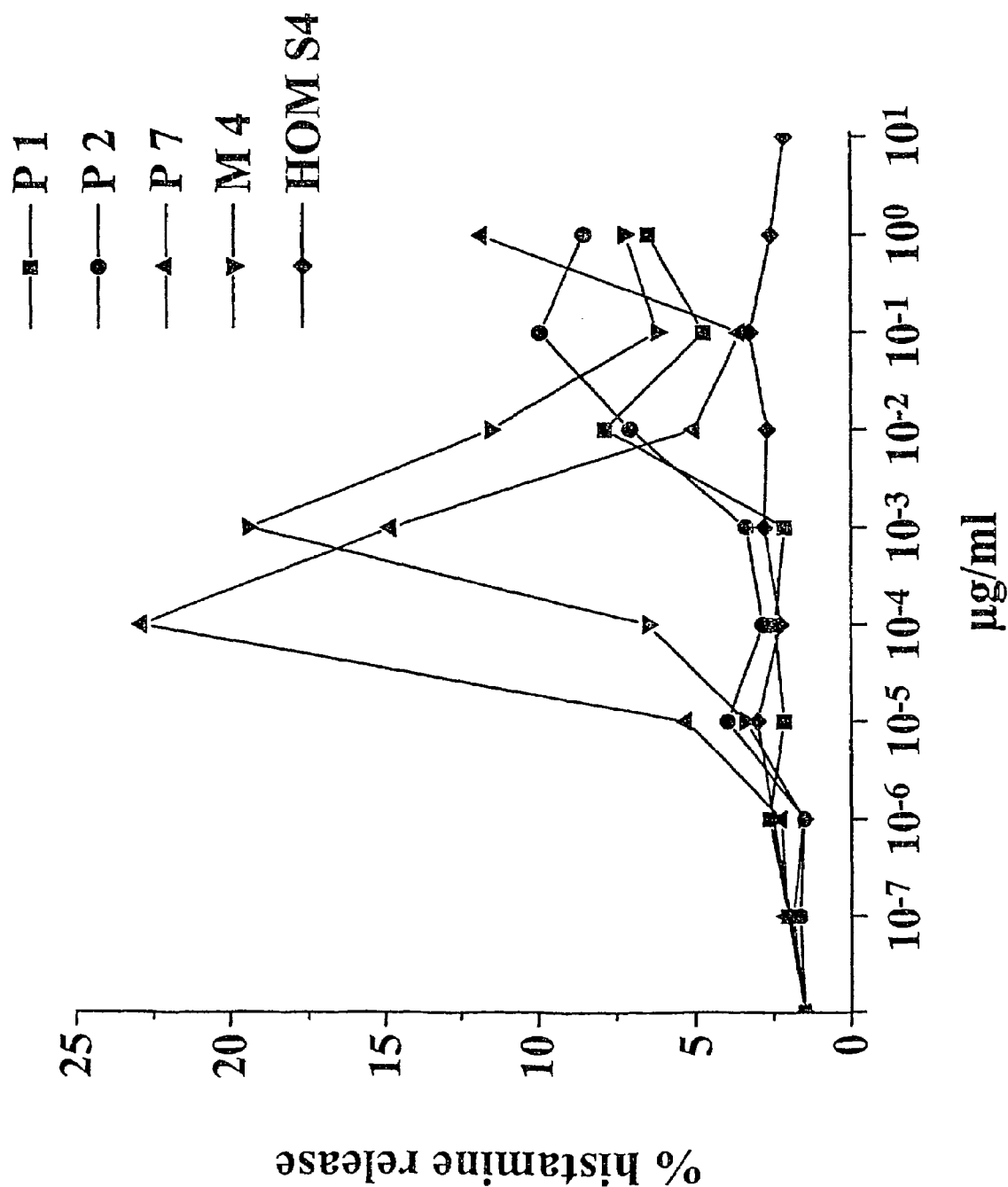

FIG. 3A, B. Induction of histamine release from basophils of a timothy grass pollen allergic patient. Granulocytes of a timothy grass pollen allergic patient were incubated with various concentrations (x-axis) of rPhl p 7 wild type (P7), Phl p 7-derived peptides (P1, P2), Phl p 7-derived mutant (M4) or another antigen (Hom s 4) (FIG. 3A). Granulocytes of the same patient were also incubated with various concentrations (x-axis) of KLH-coupled rPhl p 7 wild type (P7-K), Phl p 7-derived peptides (P1-K, P2-K) or Phl p 7-derived mutant (M4-K) (FIG. 3B).The percentage of histamine released into the cell-free culture supernatant is displayed on the y-axis.

Figure 4:
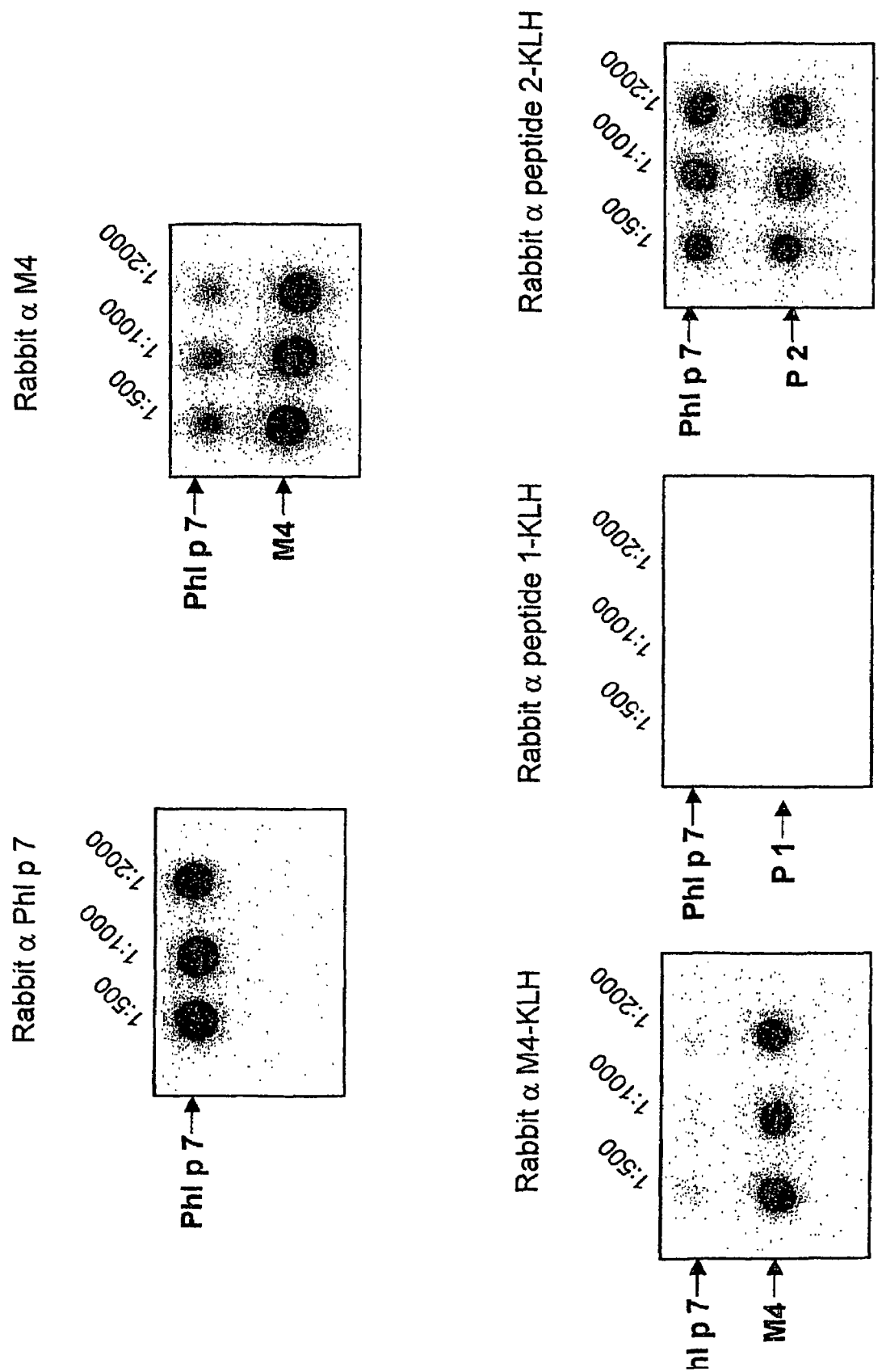

FIG. 4. Rabbit antisera against KLH-coupled peptides or against coupled and uncoupled Phl p 7-mutant react with complete Phl p 7 wild type. Nitrocellulose-dotted Phl p 7 and Phl p 7-derived peptides or mutant were probed with the corresponding rabbit antiserum in different concentrations (1:500, 1:1000, 1:2000). Bound rabbit antibodies were detected with $^{125}$I-donkey anti rabbit antibodies.

Figure 5:
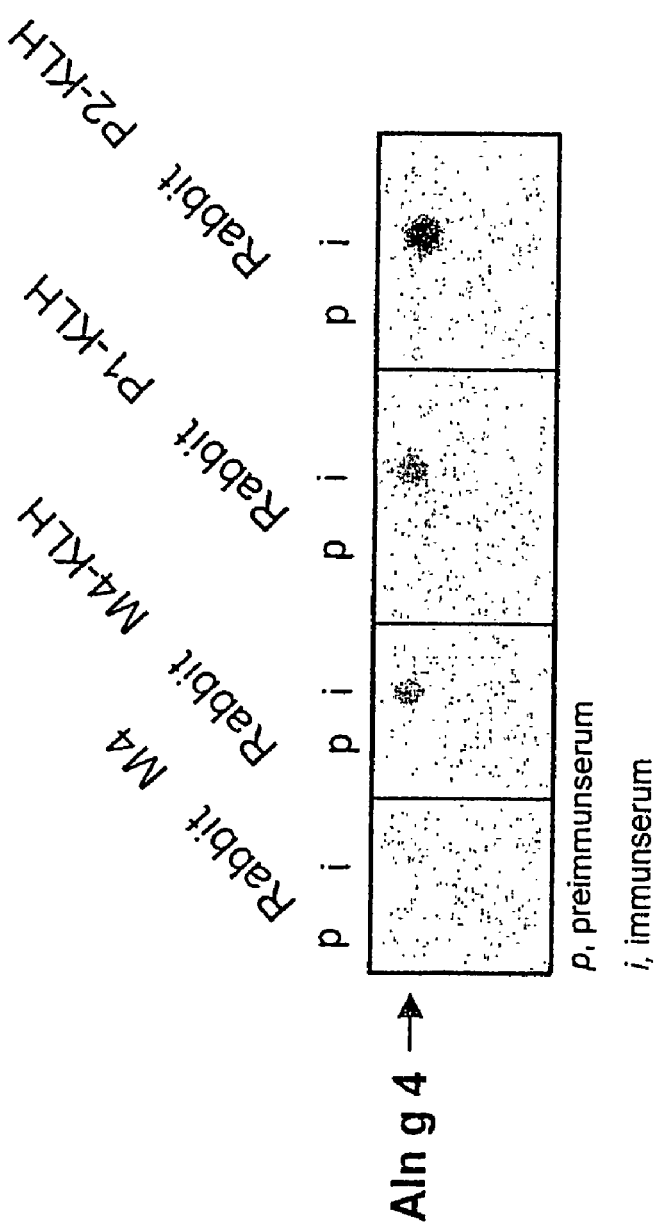

FIG. 5. Rabbit antisera against KLH-coupled peptides or against coupled and uncoupled Phl p 7-mutant react with a Phl p 7-cross-reactive calcium-binding protein from alder pollen, Aln g 4.

Nitrocellulose dotted Aln g 4 was probed with rabbit antiserum (anti-M4, anti-M4-KLH, anti-P1-KLH, anti-P2-KLH). Bound rabbit antibodies were detected with $^{125}$I-donkey anti-rabbit antibodies.

FIG. 6 (Table 1). Characteristics of two non-allergenic Phl p 7-derived synthetic peptides and three Phl p 7-derived mutants with reduced allergenicity. Position, sequence, length, molecular weight, isoelectric point and fold are displayed. Mutated amino acids are printed in bold letters. Figure discloses SEQ ID NOS: 2-6, respectively, in order of appearance.

FIG. 7 (Table 2). Immediate type skin reactions to complete rPhl p 7, Phl p 7-derived peptides and to a Phl p 7-derived mutant (M4). Three timothy grass pollen allergic patients (#1-3) and a non-allergic individual (#4) were tested. The mean wheal diameters (mm) are displayed for two different concentrations of rPhl p 7, for timothy grass pollen extract, histamine and two different concentrations of the two peptides and the mutant.

FIG. 8 (Table 3). Inhibition of rabbit anti Phl p 7 peptide and of rabbit anti Phl p 7 mutant antisera to serum IgE binding of grass pollen allergic patients to rPhl p 7.

FIG. 9. Alignment of the amino acid sequences of Phl p 7 (SEQ ID NO: 1) and Aln g 4. (SEQ ID NO: 7). Amino acid residues which may preferably be substituted or deleted in 2-EF hand pollen allergens are shown in bold.

The invention is further illustrated by the following non-limiting examples:

EXAMPLE 1

Characterization of two peptides comprising the complete N-terminal or the C-terminal calcium-binding domain of Phl p 7 and of Phl p 7-derived mutants with amino acid exchanges in the first and in the second EF-hand.

Peptide Synthesis:

Peptides were synthesized using Fmoc (9-fluorenyl-methoxycarbonyl)-strategy with HBTU (2-(1H-benzotria-zol-1-yl) 1,1,3,3 tetramethyluronium hexafluorophosphat)-activation (0.1 mmol small-scale cycles) on the Applied Biosystems peptide synthesizer Model 433A (foster City, Calif.). preloaded PEG-PS (polyethyleneglycol polysterene) resins (0.15-0.2 mmol/g loading) (per Septive Biosystems, Warrington, UK) were used as solid phase to build up the peptides. Chemicals were purchased from Applied Biosystems. Coupling of amino acids was confirmed by conductivity monitoring in a feedback control system. One cysteine residue was added to each peptide to facilitate coupling of the peptides to carriers. Peptides were cleaved from the resins with a mixture of: 250 µl dest. Water, 250 µl Triisopropylsilan (Fluka, Buchs, Switzerland), 9.5 ml TFA for 2 h and precipitated in tert-Butylmethylether (Fluka, Buchs, Switzerland). The identity of the peptides was checked by mass-spectrometry and they were purified to >90% purity by preparative HPLC (PiChem, Graz, Austria).

Generation, Expression and Purification of a Phl p 7-Derived Mutants:

Point mutations were introduced into the cDNA of Phl p 7, cloned into the expression vector pET17b, using a Chameleon double-stranded site-directed mutagenesis kit (Stratagene, East Kew, Australia). Specific primers were designed to mutate Phl p 7 at specific sites. The following mutations were made: Mutant 1.6 (SEQ ID NO:4): 24E→24A (first EF-hand); 59E→59A (second EF-hand). Mutant 2A (SEQ ID NO:5): 17D→A, 24E→24A (first EF-hand); 59E→59A (second EF-hand). Mutant 4 (SEQ ID NO:6): 17D→A, 24E→24A (first EF-hand); 52D→52A, 59E→59A (second EF-hand). The recombinant Phl p 7-derived mutants were expressed in Escherichia coli BL21 (DE3). E. coli were grown to an $OD_{600}$ of 0.4 in LB-medium containing 100 mg/l ampicillin. The expression of recombinant proteins was induced by adding isopropyl-β-thiogalactopyranoside to a final concentration of 1 mM and culturing for additional 4 hours at 37° C. E. coli cells from a 500 ml culture were harvested by centrifugation, resuspended in 10 ml PBS and homogenized using an ultraturrax (Ika, Heidelberg, Germany). A fraction containing soluble proteins was obtained after centrifugation of the homogenate at 10.000 rpm (Sorval, RC5C, SS34 rotor) for 30 min at 4° C. Enrichment of the protein in the soluble fraction and removal of contaminating proteins were achieved by addition of 70% w/v ammonsulfate to the soluble E.coli fraction and centrifugation (18.000 rpm, Sorval SS34, 4° C., 30 min.). The soluble Phl p 7-derived mutant fraction was dialyzed against water, lyophilized, resuspended in 50 ml buffer A (25 mM Imidazole, 1 mM β-mercaptoethanol, pH=7.4), and applied to a DEAE anion exchange column (Pharmacia, Uppsala, Sweden). The mutant was eluted by a NaCl gradient (buffer A containing 500 mM NaCl) at ~200 mM NaCl. Fractions containing pure Phl p 7-derived mutant were pooled, dialyzed against water, and lyophilized. Protein samples were analyzed for purity by sodium dodecyl sulfate-polyacrylamide gel electrophoresis (SDS-PAGE) and protein staining.

Coupling of Peptides and Mutant (M4) to KLH

HPLC-purified peptides or Phl p 7-derived mutant as well as Phl p 7 wild type were coupled to KLH (keyhole limpet hemocyanin, MW $4.5 \times 10^3 - 1.3 \times 10^7$, Pierce, Rockford, Ill.) according to the manufacturers advice and purified using a Conjugation kit (Sigma, St. Louis).

Secondary Structure Analysis (CD)

CD measurements were carried out on a Jasco J-715 spectropolarimeter using a 0.1 cm pathlength cell equilibrated at 20° C. Spectra were recorded with 0.5 nm resolution at a scan speed of 100 nm/min and resulted from averaging 3 scans. The final spectra were baseline-corrected by subtracting the corresponding MilliQ spectra obtained under identical conditions. Results were fitted with the secondary structure estimation program J-700.

The far-UV spectra indicate, that the point mutants contain considerable amount of α-helical structure. The spectra are characterized by minima at 224 and 208 nm and a strong maximum below 200 nm. The a-helical content is identical for the various point mutations. The native recombinant Phl p 7 showed a significant larger α-helical signal. A second analysis comparing Phl p 7 and point mutant-4 revealed, that—in contrast to the normalized spectrum of rPhl p 7 the signal for mutant-4 significantly decreased by approximately 20%. Furthermore the minimum at 208 nm is slightly shifted to a smaller wavelength and the zero-crossing of the curve is below 200 nm. These findings are indicative for an increasing portion of random-coil secondary structure within the mutant-4 protein.

The N-terminal peptide exhibited a random coil secondary structure, with characteristic minima at 200 and 225 nm. This points to the fact, that truncation of intact rPhl p 7 protein not only leads to the disruption of the overall assembly, but furthermore affects the fold of the single EF-hand domain. This could also be seen for the corresponding C-terminal peptide, as this protein was not only unfolded, but furthermore displayed a significant decreased solubility and precipitation.

EXAMPLE 2

Fragmentation of Phl p 7 at specific sites leads to loss of IgE binding capacity, mutation of Phl p 7 at specific sites of the calcium-binding domains leads to decreased IgE binding capacity.

a) The Phl p 7-Derived Mutants and Phl p 7-Derived Peptides Show Reduced IgE Binding:

The IgE binding capacity of purified Phl p 7-derived mutants (M1.6, M2A, M4) was compared with that of Phl p 7 wild type by western blot analysis using serum from a timothy grass pollen allergic patient (FIG. 2A) as well as by dot blot experiments using sera from ten timothy grass pollen allergic patients (FIG. 2B). The western blot analysis showed a reduced IgE binding capacity for all mutants compared to Phl p 7. The strongest reduction was detected for the mutant M4 (FIG. 2A). This finding was confirmed by the dot blot experiments: only four out of ten patients showed weak IgE binding to M4, five out of ten reacted with M2A, six out of ten with M1.6 (FIG. 2B). The double mutant (M4) hence exhibited the strongest reduction of IgE binding capacity.

The IgE binding capacity of Phl p 7-derived peptides was compared with that of Phl p 7 wild type by dot blot experiments using sera from ten timothy grass pollen allergic patients (FIG. 2B). For both peptides the IgE binding capacity was completely abolished, when tested with serum from ten timothy grass pollen allergic patients.

b) Reduced Basophil Histamine Release by Phl p 7 Mutant and Peptides

Next the Phl p 7-derived peptides and the Phl p 7-derived mutant were compared with Phl p 7 wild type for their capacity to induce histamine release from basophils of a timothy grass pollen allergic individual.

Granulocytes were isolated from heparinized blood samples of a timothy grass pollen allergic individual by dextran sedimentation. Cells were incubated with increasing concentrations ($10^{-6}$-10 µg/ml) of each peptide or the mutant, and, for control purposes, with rPhl p 7 wild type. Histamine released in the cell-free culture supernatant was measured by radioimmunoassay (Immunotech, Marseille, France). Total histamine was determined after freezing and thawing of the cells. Results are displayed as mean values of triplicate determinations.

Figure 3B:
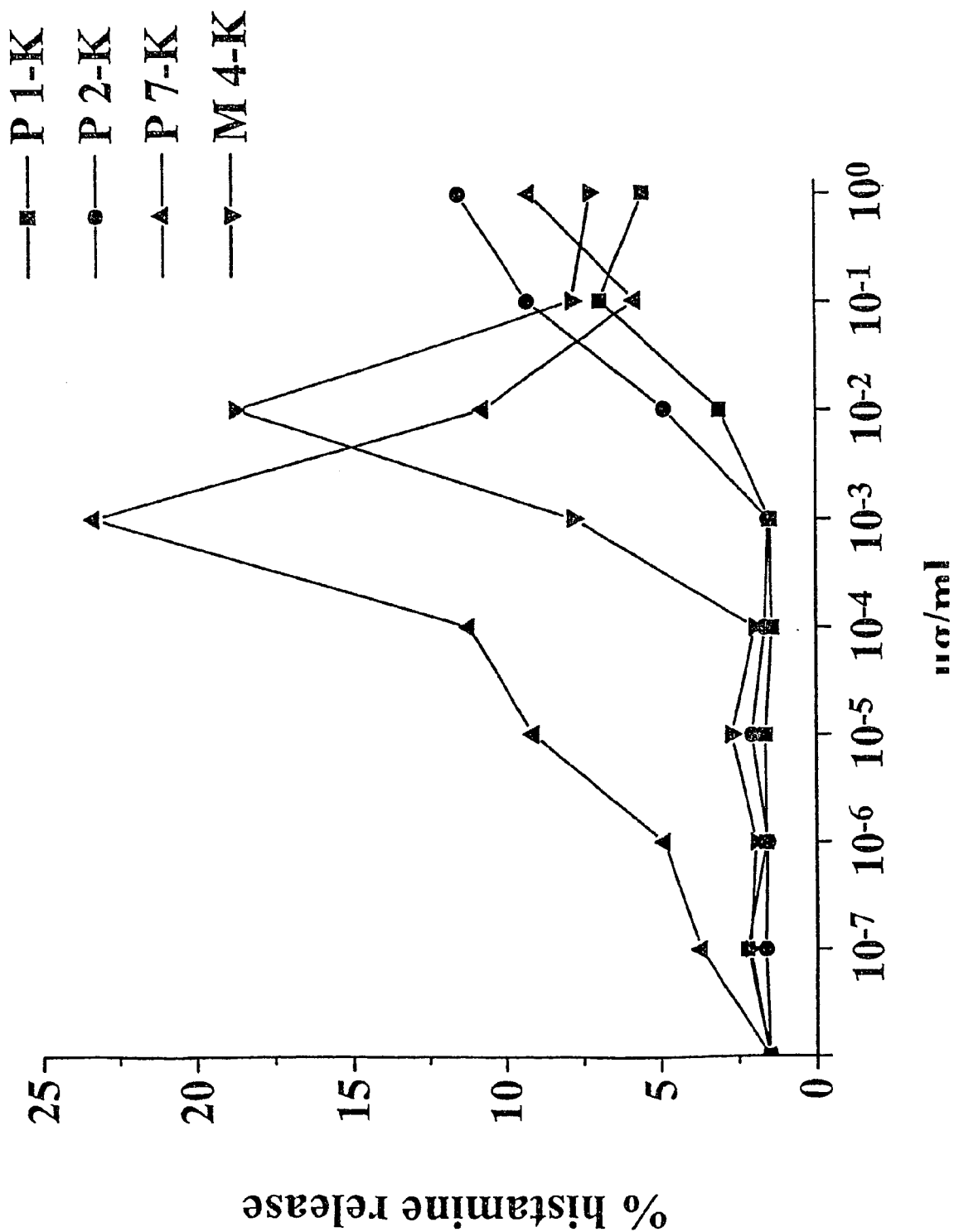

As exemplified in FIG. 3 it was found that none of the peptides (coupled or uncoupled) induced histamine release up to an concentration of $10^{-3}$ µg/ml. The Phl p 7-derived mutant M4 induced a dose-dependent release of histamine with a maximum release at a concentration of $10^{-3}$ µg/ml, whereas Phl p 7 wild type induced a maximum histamine release already at a concentration at $10^{-4}$ µg/ml. Coupling to KLH did not increase the allergenic activity of the mutant and peptides (FIG. 3B).

c) Reduced Allergenic In Vivo Activity of the Mutant and the Peptides

In vivo testing in timothy grass pollen allergic patients confirmed the abolished allergenic activity of the Phl p 7-derived peptides and the reduced allergenicity of the Phl p 7-derived mutant M4.

The in vivo allergenic activity of the peptides and the mutant was studied by skin prick testing (SPT) in 3 timothy grass pollen allergic patients and a non-atopic individual. SPTs were performed on the individuals' forearms. Twenty microliter aliquots containing 2 concentrations of complete rPhl p 7 or Phl p 7-derived mutant M4 (2 µg/ml, 8 µg/ml) as well as two concentrations of Phl p 7-derived peptides (1 µg/ml m, 4 µg/ml ) were applied. In addition, standardized skin prick solutions (timothy grass pollen extract and histamine) (Allergopharma, Reinbeck, Germany) were tested. Reactions were recorded 20 minutes after SPT by photography and by transferring the ballpoint pen-surrounded wheal area with a scotch tape to paper. The mean wheal diameter (Dm) was calculated by measuring the maximal longitudinal and transversal diameter and dividing their sum by 2.

Skin prick tests were performed in 3 timothy grass pollen allergic patients and a non-allergic individual with rPhl p 7, Phl p 7-derived peptides and a Phl p 7-derived mutant M4 (Table 3). None of the peptides induced any immediate skin reactions when applied at a concentration of 4 µg/ml, whereas Phl p 7 wild type already induced immediate type skin reactions at a concentration of 2 µg/ml. M4 induced immediate skin reactions that were moderately weaker than those induced by Phl p 7 wild type (mean wheal diameter induced by Phl p 7 at a concentration of 8 µg/ml: 9.3 mm; mean wheal diameter induced by M4 at a concentration of 8 µg/ml: 7 mm). All timothy grass pollen allergic patients displayed immediate skin reactions to timothy grass pollen extract. The non-allergic individual showed no reactions to timothy grass pollen extract, rPhl p 7, the Phl p 7-derived peptides or the Phl p 7-derived mutant (Table 3:#4). All individuals reacted after testing with histamine, used as a positive control (Table 3).

EXAMPLE 3

Immunization with Phl p 7-derived peptides and the Phl p 7-derived mutant induces IgG antibodies that recognize rPhl p 7 wild type as well as a cross-reactive allergen from alder, Aln g 4.

In order to test whether immunization with Phl p 7-derived peptides or Phl p 7-derived mutant M4 will induce IgG antibodies that react with complete Phl p 7 molecule and Phl p 7 cross-reactive allergens, rabbits were immunized with Phl p 7 wild type, the peptides or the Phl p 7-mutant as well as with KLH-conjugated peptides/proteins using Freund's adjuvant. Eight rabbits were immunized with a peptide-KLH conjugate, the mutant-KLH conjugat, Phl p 7-KLH conjugate, unconjugated peptides, mutant and Phl p 7 wild type, respectively, (200 µg/injection) using Freund's complete and incomplete adjuvants (Charles River, Kibllegg, Germany). Serum samples were obtained in four week intervals. Sera were stored at −20° C. until analysis.

Reactivity of peptide-induced IgG antibodies and Phl p 7-mutant-induced IgG antibodies to rPhl p 7 wild type and a cross reactive allergen was studied by dot blot experiments. Phl p 7 wild type as well as the corresponding immunogen (peptide 1, peptide 2, Mut-4) were dotted onto nitrocellulose-strips (1 µg/dot). Strips were exposed to different dilutions of rabbit antiserum (1:500, 1:1000, 1:2000).

Similarly, recombinant Aln g 4, a Phl p 7-cross-reactive calcium-binding allergen from alder, was dotted onto nitrocellulose and strips were exposed to 1:1000 diluted rabbit antiserum. Bound rabbit antibodies were detected with a 1:1000 diluted $^{125}$I-labeled donkey anti-rabbit antiserum (Amersham Pharmacia Biotech).

The peptides coupled to KLH induced IgG anti-Phl p 7 antibody responses (FIG. 4), as well as the Phl p 7-derived mutant (M4, coupled and uncoupled). Similarly, rabbit antisera raised against M4, M4-KLH and the coupled peptides recognized the Phl p 7-cross-reactive allergen, Aln g 4 (FIG. 5).

EXAMPLE 4

Anti-peptide and anti-mutant antisera inhibit the binding of serum IgE from grass pollen allergic patients to complete rPhl p 7.

The capacity of anti-Phl p 7 peptide and anti-Phl p 7 mutant antibodies to inhibit the binding of allergic patients' serum IgE to complete rPhl p 7 was studied by ELISA competition using sera from four grass pollen allergic patients (Table 3).

The ability of peptide or mutant-induced rabbit IgG to inhibit the binding of allergic patients' IgE to complete Phl p 7 was investigated by ELISA competition assay. ELISA plates (Nunc Maxisorp, Rokslide, Denmark) were coated with rPhl p 7 (1 µg/ml) and preincubated either with a 1:250 dilution of each of the anti-peptide antisera (anti-P1-KLH, anti-P2-KLH), the anti-mutant antiserum (anti-M 4-KLH) and, for control purposes, with the corresponding preimmunserum. After washing plates were incubated with 1:3 diluted sera from four Phl p 7-sensitized grass pollen allergic patients and bound IgE antibodies were detected with a monoclonal rat anti-human IgE antibody (Pharmingen, San Diego, Calif.), diluted 1:1000, followed by a 1:2000 diluted HRP-coupled sheep anti rat Ig antiserum (Amersham Pharmacia Biotech, Uppsala, Sweden). The percentage inhibition of IgE binding achieved by preincubation with the anti-peptide or anti-mutant antisera was calculated as follows: % inhibition of IgE binding=100-OD$_I$/OD$_P$×100. OD$_I$ and OD$_P$ represent the extinctions after preincubation with the rabbits immune and preimmune serum, respectively.

Strongest inhibition of IgE binding was observed after preincubation with anti-peptide 2 (47% average inhibition). Anti-mutant-KLH coupled antibodies exhibited a lower capacity to inhibit serum IgE binding to Phl p 7 (23.4% average inhibition). Inhibition of serum IgE binding after preincubation with anti-mutant could be detected in two out of four sera (average inhibition 5.6%) and in only one out of four sera after preincubation with anti-peptide 1.

This application claims priority to EP 02021837.6, filed Sep. 27, 2002, the entirety of which is hereby incorporated by reference.

The invention claimed is:

1. A mutated polypeptide derived from the pollen allergen Phl p 7, said polypeptide selected from the group consisting of the sequences of SEQ ID NO:2, SEQ ID NO:3, SEQ ID NO:4, SEQ ID NO:5, and SEQ ID NO:6, whereby said polypeptide has a reduced allergenic activity compared to wild type Phl p 7.

2. A polypeptide according to claim 1 which is capable of inducing an IgG response in a mammal.

3. A polypeptide according to claim 1 or 2 which induces a histamine release which is significantly reduced compared with wild type Phl p 7.

4. A pharmaceutical composition comprising a polypeptide according to claim 1 and a pharmaceutically acceptable carrier or diluent.

5. A kit comprising a polypeptide according to claim 1 and a pharmaceutically acceptable carrier or diluent.

* * * * *

SEQUENCE LISTING

```
<160> NUMBER OF SEQ ID NOS: 11

<210> SEQ ID NO 1
<211> LENGTH: 78
<212> TYPE: PRT
<213> ORGANISM: Phleum pratense

<400> SEQUENCE: 1

Met Ala Asp Asp Met Glu Arg Ile Phe Lys Arg Phe Asp Thr Asn Gly
1               5                   10                  15

Asp Gly Lys Ile Ser Leu Ser Glu Leu Thr Asp Ala Leu Arg Thr Leu
            20                  25                  30

Gly Ser Thr Ser Ala Asp Glu Val Gln Arg Met Met Ala Glu Ile Asp
        35                  40                  45

Thr Asp Gly Asp Gly Phe Ile Asp Phe Asn Glu Phe Ile Ser Phe Cys
    50                  55                  60

Asn Ala Asn Pro Gly Leu Met Lys Asp Val Ala Lys Val Phe
65                  70                  75

<210> SEQ ID NO 2
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Asp Asp Met Glu Arg Ile Phe Lys Arg Phe Asp Thr Asn Gly Asp
1               5                   10                  15

Gly Lys Ile Ser Leu Ser Glu Leu Thr Asp Ala Leu Arg Thr Leu Gly
            20                  25                  30

Ser Thr Ser Ala
        35

<210> SEQ ID NO 3
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Ala Asp Glu Val Gln Arg Met Met Ala Glu Ile Asp Thr Asp Gly
1               5                   10                  15

Asp Gly Phe Ile Asp Phe Asn Glu Phe Ile Ser Phe Cys Asn Ala Asn
            20                  25                  30

Pro Gly Leu Met Lys Asp Val Ala Lys Val Phe
        35                  40

<210> SEQ ID NO 4
```

<211> LENGTH: 78
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Met Ala Asp Asp Met Glu Arg Ile Phe Lys Arg Phe Asp Thr Asn Gly
1               5                   10                  15

Asp Gly Lys Ile Ser Leu Ser Ala Leu Thr Asp Ala Leu Arg Thr Leu
            20                  25                  30

Gly Ser Thr Ser Ala Asp Glu Val Gln Arg Met Met Ala Glu Ile Asp
        35                  40                  45

Thr Asp Gly Asp Gly Phe Ile Asp Phe Asn Ala Phe Ile Ser Phe Cys
    50                  55                  60

Asn Ala Asn Pro Gly Leu Met Lys Asp Val Ala Lys Val Phe
65                  70                  75

<210> SEQ ID NO 5
<211> LENGTH: 78
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Met Ala Asp Asp Met Glu Arg Ile Phe Lys Arg Phe Asp Thr Asn Gly
1               5                   10                  15

Ala Gly Lys Ile Ser Leu Ser Ala Leu Thr Asp Ala Leu Arg Thr Leu
            20                  25                  30

Gly Ser Thr Ser Ala Asp Glu Val Gln Arg Met Met Ala Glu Ile Asp
        35                  40                  45

Thr Asp Gly Asp Gly Phe Ile Asp Phe Asn Ala Phe Ile Ser Phe Cys
    50                  55                  60

Asn Ala Asn Pro Gly Leu Met Lys Asp Val Ala Lys Val Phe
65                  70                  75

<210> SEQ ID NO 6
<211> LENGTH: 78
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Met Ala Asp Asp Met Glu Arg Ile Phe Lys Arg Phe Asp Thr Asn Gly
1               5                   10                  15

Ala Gly Lys Ile Ser Leu Ser Ala Leu Thr Asp Ala Leu Arg Thr Leu
            20                  25                  30

Gly Ser Thr Ser Ala Asp Glu Val Gln Arg Met Met Ala Glu Ile Asp
        35                  40                  45

Thr Asp Gly Ala Gly Phe Ile Asp Phe Asn Ala Phe Ile Ser Phe Cys
    50                  55                  60

Asn Ala Asn Pro Gly Leu Met Lys Asp Val Ala Lys Val Phe
65                  70                  75

<210> SEQ ID NO 7
<211> LENGTH: 85

<212> TYPE: PRT
<213> ORGANISM: Alnus glutinosa

<400> SEQUENCE: 7

Met Ala Asp Asp His Pro Gln Asp Gln Ala Glu His Glu Arg Ile Phe
1               5                   10                  15

Lys Cys Phe Asp Ala Asn Gly Asp Gly Lys Ile Ser Ala Ser Glu Leu
            20                  25                  30

Gly Asp Ala Leu Lys Thr Leu Gly Ser Val Thr Pro Asp Glu Val Lys
        35                  40                  45

His Met Met Ala Glu Ile Asp Thr Asp Gly Asp Gly Phe Ile Ser Phe
50                  55                  60

Gln Glu Phe Thr Asn Phe Ala Arg Ala Asn Arg Gly Leu Val Lys Asp
65                  70                  75                  80

Val Ala Lys Ile Phe
                85

<210> SEQ ID NO 8
<211> LENGTH: 80
<212> TYPE: PRT
<213> ORGANISM: Cynodon dactylon

<400> SEQUENCE: 8

Met Ala Asp Thr Gly Asp Met Glu His Ile Phe Lys Arg Phe Asp Thr
1               5                   10                  15

Asn Gly Asp Gly Lys Ile Ser Leu Ala Glu Leu Thr Asp Ala Leu Arg
            20                  25                  30

Thr Leu Gly Ser Thr Ser Ala Asp Glu Val Gln Arg Met Met Ala Glu
        35                  40                  45

Ile Asp Thr Asp Gly Asp Gly Phe Ile Asp Phe Asp Glu Phe Ile Ser
50                  55                  60

Phe Cys Asn Ala Asn Pro Gly Leu Met Lys Asp Val Ala Lys Val Phe
65                  70                  75                  80

<210> SEQ ID NO 9
<211> LENGTH: 84
<212> TYPE: PRT
<213> ORGANISM: Olea europaea

<400> SEQUENCE: 9

Met Ala Asp Asp Pro Gln Glu Val Ala Glu His Glu Arg Ile Phe Lys
1               5                   10                  15

Arg Phe Asp Ala Asn Gly Asp Gly Lys Ile Ser Ser Ser Glu Leu Gly
            20                  25                  30

Glu Thr Leu Lys Thr Leu Gly Ser Val Thr Pro Glu Glu Ile Gln Arg
        35                  40                  45

Met Met Ala Glu Ile Asp Thr Asp Gly Asp Gly Phe Ile Ser Phe Glu
50                  55                  60

Glu Phe Thr Val Phe Ala Arg Ala Asn Arg Gly Leu Val Lys Asp Val
65                  70                  75                  80

Ala Lys Ile Phe

<210> SEQ ID NO 10
<211> LENGTH: 85
<212> TYPE: PRT
<213> ORGANISM: Betula pendula

<400> SEQUENCE: 10

```
Met Ala Asp Asp His Pro Gln Asp Lys Ala Glu Arg Glu Arg Ile Phe
1               5                   10                  15

Lys Arg Phe Asp Ala Asn Gly Asp Gly Lys Ile Ser Ala Ala Glu Leu
                20                  25                  30

Gly Glu Ala Leu Lys Thr Leu Gly Ser Ile Thr Pro Asp Glu Val Lys
                35                  40                  45

His Met Met Ala Glu Ile Asp Thr Asp Gly Asp Gly Phe Ile Ser Phe
            50                  55                  60

Gln Glu Phe Thr Asp Phe Gly Arg Ala Asn Arg Gly Leu Leu Lys Asp
65                  70                  75                  80

Val Ala Lys Ile Phe
                85

<210> SEQ ID NO 11
<211> LENGTH: 79
<212> TYPE: PRT
<213> ORGANISM: Brassica rapa

<400> SEQUENCE: 11

Met Ala Asp Ala Glu His Glu Arg Ile Phe Lys Lys Phe Asp Thr Asp
1               5                   10                  15

Gly Asp Gly Lys Ile Ser Ala Ala Glu Leu Glu Glu Ala Leu Lys Lys
                20                  25                  30

Leu Gly Ser Val Thr Pro Asp Asp Val Thr Arg Met Met Ala Lys Ile
                35                  40                  45

Asp Thr Asp Gly Asp Gly Asn Ile Ser Phe Gln Glu Phe Thr Glu Phe
            50                  55                  60

Ala Ser Ala Asn Pro Gly Leu Met Lys Asp Val Ala Lys Val Phe
65                  70                  75
```